US008070817B2

(12) United States Patent  (10) Patent No.: US 8,070,817 B2
Gradl et al.  (45) Date of Patent: Dec. 6, 2011

(54) VERTEBRAL IMPLANT

(75) Inventors: Georg Gradl, Börgerende (DE); Cyrus Khodadadyan-Klostermann, Detmold (DE)

(73) Assignee: M.O.R.E. Medical Solutions GmbH, Borgerende (DE)

( * ) Notice: Subject to any disclaimer, the term of this patent is extended or adjusted under 35 U.S.C. 154(b) by 332 days.

(21) Appl. No.: 11/823,467

(22) Filed: Jun. 27, 2007

(65) Prior Publication Data
US 2008/0015704 A1  Jan. 17, 2008

(30) Foreign Application Priority Data

Jun. 28, 2006 (DE) .................. 10 2006 030 124

(51) Int. Cl.
*A61F 2/44* (2006.01)
(52) U.S. Cl. .......................... 623/17.16; 623/17.15
(58) Field of Classification Search ..... 623/17.11–17.16
See application file for complete search history.

(56) References Cited

U.S. PATENT DOCUMENTS

| 5,236,460 | A | * | 8/1993 | Barber | 623/17.15 |
| 5,360,430 | A | * | 11/1994 | Lin | 606/247 |
| 5,534,029 | A | * | 7/1996 | Shima | 623/17.15 |
| 5,562,738 | A | | 10/1996 | Boyd et al. | 623/17 |
| 5,702,455 | A | * | 12/1997 | Saggar | 623/17.15 |
| 5,916,267 | A | * | 6/1999 | Tienboon | 623/17.11 |
| 6,015,436 | A | * | 1/2000 | Schonhoffer | 623/17.16 |
| 6,176,881 | B1 | * | 1/2001 | Schar et al. | 623/17.11 |
| 6,190,413 | B1 | * | 2/2001 | Sutcliffe | 623/17.11 |
| 6,193,755 | B1 | * | 2/2001 | Metz-Stavenhagen et al. | 623/17.11 |
| 6,200,348 | B1 | | 3/2001 | Biedermann et al. | 623/17.11 |
| 6,616,695 | B1 | * | 9/2003 | Crozet et al. | 623/17.11 |
| 6,866,682 | B1 | * | 3/2005 | An et al. | 623/17.15 |
| 6,908,485 | B2 | | 6/2005 | Crozet et al. | 623/17.11 |
| 7,402,176 | B2 | | 7/2008 | Malek | 623/17.16 |
| 2003/0045877 | A1 | * | 3/2003 | Yeh | 606/61 |
| 2004/0049271 | A1 | | 3/2004 | Biedermann | |
| 2004/0167626 | A1 | | 8/2004 | Geremakis et al. | 623/17.15 |
| 2004/0210312 | A1 | * | 10/2004 | Neumann | 623/17.11 |
| 2005/0004572 | A1 | | 1/2005 | Biedermann et al. | 606/61 |
| 2005/0060036 | A1 | | 3/2005 | Schultz | |
| 2005/0113921 | A1 | | 5/2005 | An | |
| 2005/0261769 | A1 | | 11/2005 | Moskowitz et al. | 623/17.11 |
| 2008/0133013 | A1 | * | 6/2008 | Duggal et al. | 623/17.16 |

FOREIGN PATENT DOCUMENTS

| CA | 2 216 450 | 5/2004 |
| DE | 198 56 013 | 6/2000 |
| WO | WO 0033752 | 6/2000 |

* cited by examiner

*Primary Examiner* — Eduardo C Robert
*Assistant Examiner* — Jerry Cumberledge
(74) *Attorney, Agent, or Firm* — Andrew Wilford

(57) ABSTRACT

An implant for insertion between a pair of spaced vertebrae has two interfitted parts relatively shiftable along an axis and having outer ends turned axially away from each other and each formed with an axially outwardly directed part-spherical convex surface. Formations such as a screwthread engaged between the parts can axially shift them relative to each other and lock their axial positions relative to each other. Respective L-shaped mounting brackets each have one leg extending transversely across the axis and formed with a part-spherical concave seat complementary to and fitting with a respective one of the part outer ends and another leg extending generally axially outward. The brackets are adapted to be fitted to the vertebrae. Fasteners secure each of the other legs to the respective vertebra.

7 Claims, 2 Drawing Sheets

VERTEBRAL IMPLANT

FIELD OF THE INVENTION

The present invention relates to a vertebral implant. More particularly this invention concerns such an implant for replacing a vertebra of the spinal column.

BACKGROUND OF THE INVENTION

When a vertebra is broken or crushed it is frequently necessary to ablate the body of the crushed or broken vertebra or vertebrae, normally along with the flanking disks. In order, however, to prevent the spinal column from collapsing with damage to the fragile spinal cord running in the vertebral foramen forward of the vertebral body, it is necessary to employ an implanted spacer. This device is braced vertically between the bodies of the adjacent vertebra and holds them apart at the desired spacing. It may even serve to distract two vertebrae which have become too closely spaced due to crushing of a vertebra or disk.

To this end as described in US 2004/0049271, US 2005/0113921, U.S. Pat. No. 6,015,436, and CA 2,216,450 the implant has two parts that can be moved and locked relative to each other along an axis extending between the two disks. This way the implant can be shortened and fitted in place by the surgeon, then extended to lock in place and even distract the adjacent vertebrae.

Frequently after insertion the implant is intended to become fused in place, creating a region including itself and the two adjacent vertebra where the spine is completely rigid. This constitutes a disability that is normally considered more desirable than the condition the implant was inserted to treat.

It has been suggested, however, in US 2004/0210312 and 2005/0060036 to provide some degree of movement in the implant. This eliminates the complete rigidity otherwise produced, but such implants are complex to install and not normally considered a safe treatment for an active person.

OBJECTS OF THE INVENTION

It is therefore an object of the present invention to provide an improved vertebral implant.

Another object is the provision of such an improved vertebral implant that overcomes the above-given disadvantages, in particular that fully maintains the distractibility of the two parts in order to preserve mobility in the affected segments of the spinal column.

SUMMARY OF THE INVENTION

An implant for insertion between a pair of spaced vertebrae has according to the invention two interfitted parts relatively shiftable along an axis and having outer ends turned axially away from each other and each formed with an axially outwardly directed part-spherical convex surface. Formations such as a screwthread engaged between the parts can axially shift them relative to each other and lock their axial positions relative to each other. Respective L-shaped mounting brackets each have one leg extending transversely across the axis and formed with a part-spherical concave seat complementary to and fitting with a respective one of the part outer ends and another leg extending generally axially outward. The brackets are adapted to be fitted to the vertebrae. Fasteners secure each of the other legs to the respective vertebra.

Thus according to the invention the mounting brackets are each attached to a respective one of the vertebrae and each have a curved bearing seat that engages one of the parts having a correspondingly curved bearing surface.

As a result of this design, first of all a mounting bracket is provided between the one part and the vertebra, which for achieving the desired mobility allows a relative motion of the part with respect to the mounting bracket. Hence it is not necessary to move the part itself relative to the vertebra and in direct contact with same. The mounting bracket may therefore be permanently and stably attached to the vertebra, and thus via the part allows force to be introduced over a large area with a low surface pressure in order to avoid damaging the vertebra itself. This mobility provided in the spinal column is achieved by moving the part relative to the bearing seat, thereby allowing the desired tilting motions due to the fact that the mutually contacting surfaces of the bearing seat and part roll off one another as a result of the curvature of these correspondingly shaped surfaces. The mobility between the vertebrae adjoining the space may be achieved in principle by a bearing seat cooperating with a bearing surface. It is within the scope of the invention, and in fact is particularly preferred for two mounting brackets to be provided, one mounting bracket being attached to each of the vertebrae, and for each of the parts to have a curved bearing surface which corresponds to the associated bearing seat. This design achieves mobility at the edges of the space and prevents high bending stresses from occurring in the one vertebra or the adjacent part.

Furthermore, within the scope of the invention the design is chosen so that the bearing seat has a concave curvature and the bearing surface has a convex curvature, so that the two parts together with the two bearing seats result in a type of ball-and-socket joint which permits mobility not only about a specified rotational axis, but also allows tilting motions as well as rotary motions of the spinal column.

When the radius of curvature of the bearing surface is the same for both of the parts, translation between the two bearing seats, and thus increased introduction of force into one of the bearing seats, is avoided.

To achieve a secure seat for the bearing shell on the vertebra, the long bracket leg formed with the bearing has on its side contacting the vertebra at least one tooth, it being preferred when the tooth has a beveled edge and is provided in a plurality. The teeth may be situated on a circle so that a uniform introduction of force into the vertebra is achieved on the circumference of the circle. In addition, for securely attaching the bearing shell to the vertebra the mounting bracket has a tab on the side facing away from the bearing seat for laterally overlapping the vertebra. This tab or short leg sets is not only the lateral alignment of the mounting bracket with respect to the vehicle body, but also offers the possibility for anchoring at least one bone screw for fastening the short leg, which has at least one hole, to the respective vertebra.

As a result of the design according to the invention, in which the relative motion of the parts with respect to the vertebra is transmitted via the mounting brackets, it is possible to design the two parts in the shape of a sleeve and to connect them to one another via an internal thread and an external thread, so that, although these parts undergo relative rotation with respect to the mounting bracket during distraction, this relative rotation is not critical due to the fact that torque is not exerted directly on the vertebrae, and instead only the convex bearing surface slides over the concave bearing seat. However, in order to avoid this sliding motion during the distraction of the two parts, it has proven satisfactory to select the design in such a way that the two parts are sleeves, axially engage one inside the another, and are displaceably guided relative to one another in the axial direction. A center part or ring having an internal thread is provided, and one of the sleeves makes a threaded connection with the center ring and is overlapped by both the center ring and the other sleeve. In this embodiment, the rotary motion necessary for distraction of the implant is exerted by the center ring, the two parts being secured against twisting and being displaced relative to the center ring in the manner of a spindle.

It is also advantageous for the sleeves to have radially throughgoing holes to allow the growth of tissue into the sleeve interior, or to permit active introduction of bone grafts or bone cement.

In addition, the center ring has key openings uniformly distributed over the circumference which may be used for introducing a tool by the surgeon and for twisting the center ring. To allow the length of the implant to be permanently maintained and secured after distraction of the implant to the required length has been achieved, one of the sleeves has a threaded hole in the overlap region with the other sleeve for accommodating a locking screw.

It has proven to be advantageous for the parts and/or the mounting brackets to be made of titanium, steel, or polyetheretherketone (PEEK), the selection of titanium or PEEK in particular making it possible to do imaging using nuclear magnetic resonance tomography without interference from artifacts.

Making adjustments to the size of the vertebrae may be advantageous when the mounting bracket is changeable and fixable in its longitudinal extension, in particular when the mounting bracket has a subdivided design outside the bearing seat and has mutually adjustable components. The longitudinal extension may be easily changed by use of a telescoping design, or by a threaded rod which is seated in a threaded hole and whose position is fixed by a locking screw.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
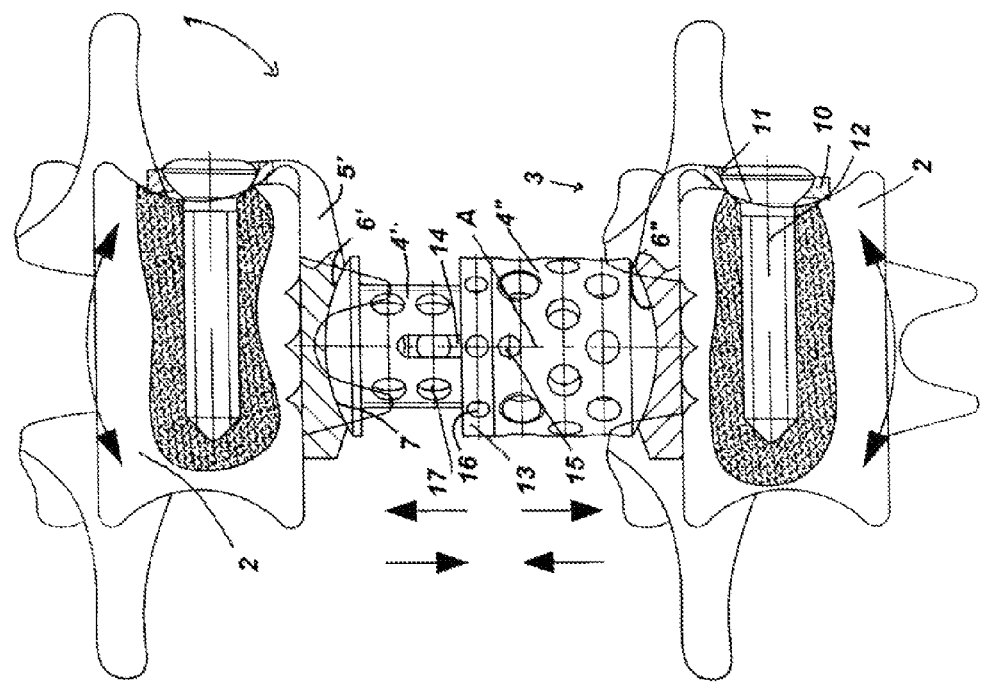
FIG. 1 is a partly sectional side view of an implant inserted into the space created by removal of a vertebra between the two remaining vertebrae.

As seen in FIG. 1 an implant 1 is intended for insertion between two vertebrae 2 of the spinal column as a placeholder for a vertebra and/or disks removed from the spinal column. This implant 1 according to the invention may also be used when a vertebra 2 has not been entirely removed from the spinal column, but instead the facet joints 3, for example, may have been retained in the spinal column. This implant 1 comprises two parts 4' and 4" which may be displaced relative to one another in the direction of their coaxial longitudinal axis A for changing the length of the implant 1. This is done by forming the two parts 4' and 4" as interfitting and coaxial cylindrical sleeves. Changing the length offers the possibility for distraction during the surgical procedure in order to adjust the length of the implant 1 to the patient's requirements.

Figure 2:
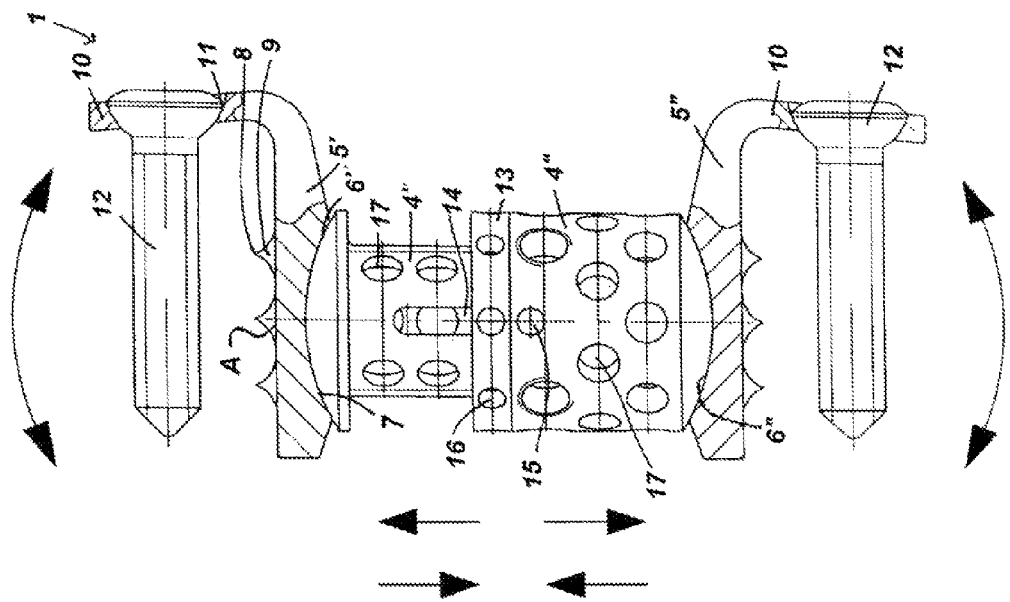
FIG. 2 is a view like 1, the vertebrae shown in FIG. 1 being omitted for clarity.
Figure 4:
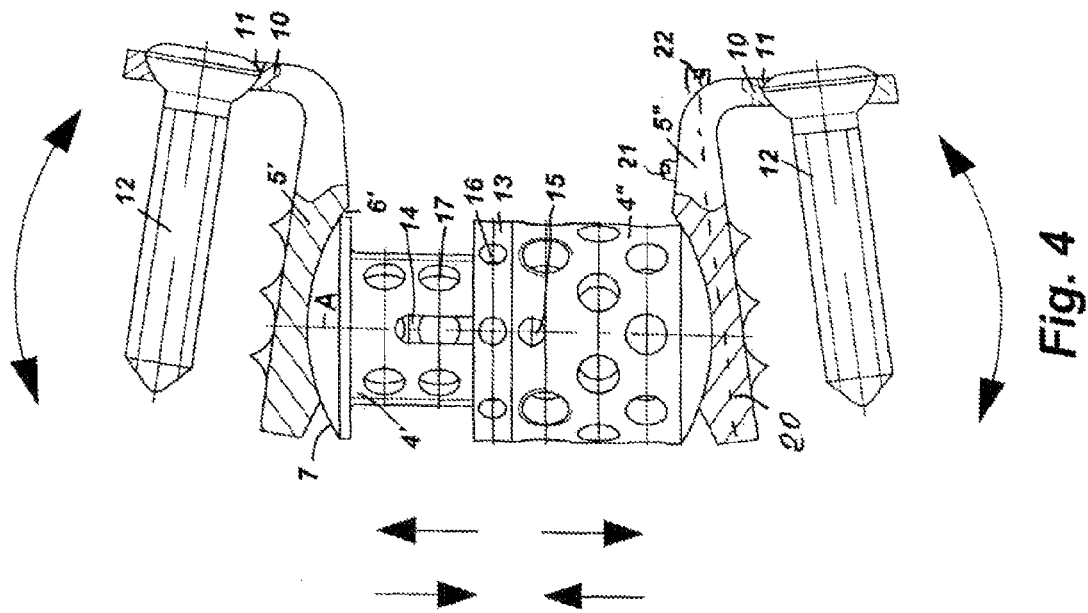
FIG. 4 is a view FIG. 2, with an opposite deflection from that shown in FIG. 3.
Figure 3:
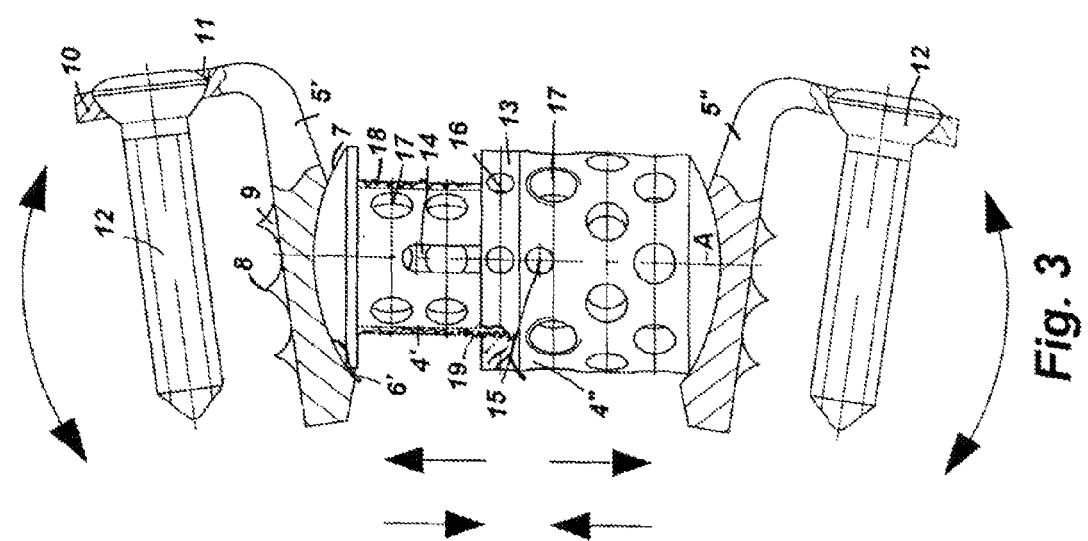
FIG. 3 is a view like FIG. 2, with a deflection from the neutral position.

As also shown in FIGS. 2-4 the implant 1 has a mounting bracket 5" that is attached to the upper vertebra 2 and that has a part-spherical and downwardly concave seat 6 that fits with a complementarily shaped upper end surface 7 of the upper element 4'. The implant 1 is similarly supported with respect to the lower vertebra 2 shown in the drawing, so that two substantially identical mounting brackets 5' and 5" with respective seats 6' and 6" are provided overall, one of the mounting brackets 5' and 5" being fastened in each of the vertebrae 2, and the lower plate 5" fitting with a lower end surface 7" of the lower part 4". The bearing seats 6' and 6" each have a concave part-spherical shape and the bearing surfaces 7' and 7" have a complementary convex shape, and the centers of curvature of the bearing surfaces 7' and 7" lie on the axis A.

The two parts 4' and 4", which have openings 17, form a rotary joint having a center of rotation located between the two bearing surfaces 7' and 7". Due to its design the rotation axis itself is not fixed, so that the implant according to the invention permits swiveling in various directions. As indicated in FIGS. 3 and 4, it is important that, to allow the natural motion sequence for curvature of the spinal column, it is not necessary for the upper vertebra 4 and the lower vertebra 4 to rotate in the same direction.

FIGS. 1-4 drawing also show that on its side contacting the vertebra 2 each mounting bracket 5' and 5" has a plurality of teeth 9, with points edges 8 arrayed in a circle centered on the axis A. These teeth 9 are used to securely anchor the mounting brackets 5' and 5" to the vertebrae 2, and in particular prevent sliding of the mounting brackets 5' and 5" with respect to the surface of the vertebrae 2. For securing the mounting brackets 5' and 5" with respect to the vertebrae 2 lateral tab 10 extending parallel to the axis A 10 is also provided extending away from the respective bearing seat 6' and 6". A cortical screw 12 engaging into the respective vertebra 2 passes through an opening 11 in each such attachment tab 11

The drawing also shows that the two parts 4' and 4" are connected to one another via an external thread 18 formed on the upper part 4' and an internal thread 19 formed on a center part or ring 13 bearing axially on the top end of the lower part 4". The upper part parts 4' engages axially inside the lower part 4" and are displaceable relative to one another axially. The parts 4' and 4" are locked against relative rotation about the axis A in a simple manner by means of a pin 15 projecting diametrally across the upper end of the lower part 4" and fitting in a pair of diametrally opposite, axially extending, and downwardly open slots 14 formed in the upper part 4". Thus, to adjust the length of the implant 1 the center ring or ring 13 is twisted by means of a wrench or key fitted to openings 16 distributed over its circumference, so that the part 4' threaded in the center ring 13 is displaced axially relative to the other part 4". After the desired distraction is achieved, a locking screw is threaded into one of the holes 16, which may be internally threaded, to fix the relative axial position of the one part 4' with respect to the other part 4" by fixing the ring 13 on the part 4'.

In order to accommodate the brackets 5' and 5" to different sizes it is possible as shown in FIG. 4 for the bracket 5" to divide the bracket along a line 20 into two parts that can slide relative to each other and that can be arrested relative to each other by a screw 21. A dovetail groove and ridge extending along the line 20 can limit such sliding to one direction. Furthermore a further screw 22 can be provided in the end to relatively shift the parts for accurate adjustment.

We claim:

1. An implant for insertion into a space between a pair of vertebrae, the implant comprising:

two interfitted cylindrical sleeves fittable in the space and, when fitted in the space, relatively slidable along an axis, the cylindrical sleeves having outer ends turned axially away from each other and each formed with an axially outwardly directed part-spherical convex end surface;

means engaged between the cylindrical sleeves for axially sliding them relative to each other and for locking their axial positions relative to each other, the means for axial shifting including a ring centered on the axis and threaded to one of the cylindrical sleeves and bearing axially on the other of the cylindrical sleeves, whereby rotation of the ring in one direction forces the two cylindrical sleeves axially apart;

respective L-shaped mounting brackets each having one leg extending transversely into the space across the axis and having an outer side directed axially away from the cylindrical sleeves and an opposite inner side directed axially toward the cylindrical sleeves and formed with a part-spherical concave seat complementary to and fitting with the outer end of the respective cylindrical sleeve, each bracket further having another leg extending outside the space generally axially outward, the brackets being adapted, when the cylindrical sleeves are fitted in the space, to be fitted to the vertebrae such that the vertebra with the respective brackets can swivel about the axis on the sleeves;

a respective circular array of teeth formed on the outer side of each of the one legs and having axially outwardly directed points adapted to engage, when the cylindrical sleeves are fitted in the space, into the respective vertebra; and a respective bone screw engaged transversely of the axis through each of the other legs when the cylindrical sleeves are fitted in the space and the brackets are fitted to the vertebra into the respective vertebra and securing each of the other legs to the respective vertebra.

2. The vertebral implant defined in claim 1, further comprising formations preventing relative rotation of the sleeves about the axis.

3. The vertebral implant defined in claim 2 wherein the formations include an axially extending slot formed on one of the sleeves and a pin fixed in the other sleeve and extending radially into the slot.

4. The vertebral implant defined in claim 3 wherein the pin extends diametrally across the other sleeve and the one sleeve is formed with two diametrally opposite such slots through which the pin passes.

5. The vertebral implant defined in claim 1 wherein the two brackets are substantially identical.

6. The vertebral implant defined in claim 1 wherein the end surfaces of the sleeves have centers of curvature lying on the axis.

7. The vertebral implant defined in claim 1 wherein each of the sleeves is formed with an array of radially throughgoing holes.

* * * * *